United States Patent
Spicci et al.

(10) Patent No.: US 11,944,491 B2
(45) Date of Patent: *Apr. 2, 2024

(54) ULTRASOUND PROBE WITH OPTIMIZED THERMAL MANAGEMENT

(71) Applicant: Esaote S.p.A., Genoa (IT)

(72) Inventors: Lorenzo Spicci, Florence (IT); Paolo Palchetti, Florence (IT); Francesca Gambineri, Pisa (IT)

(73) Assignee: Esaote S.p.A., Genoa (IT)

( * ) Notice: Subject to any disclaimer, the term of this patent is extended or adjusted under 35 U.S.C. 154(b) by 909 days.

This patent is subject to a terminal disclaimer.

(21) Appl. No.: 16/987,814

(22) Filed: Aug. 7, 2020

(65) Prior Publication Data
US 2020/0397406 A1 Dec. 24, 2020

Related U.S. Application Data

(63) Continuation of application No. 15/126,656, filed as application No. PCT/EP2015/067151 on Jul. 27, 2015, now Pat. No. 10,772,603.

(30) Foreign Application Priority Data

Sep. 2, 2014 (EP) .................................... 14183233

(51) Int. Cl.
*A61B 8/00* (2006.01)
*A61N 7/00* (2006.01)
*G10K 11/02* (2006.01)

(52) U.S. Cl.
CPC .......... *A61B 8/4444* (2013.01); *A61B 8/4281* (2013.01); *A61B 8/4483* (2013.01);
(Continued)

(58) Field of Classification Search
CPC .................................................. A61B 8/546
See application file for complete search history.

(56) References Cited

U.S. PATENT DOCUMENTS 5,402,793 A 4/1995 Gruner et al.
5,545,942 A 8/1996 Jaster et al.
(Continued)

FOREIGN PATENT DOCUMENTS

| EP | 2842642 A2 | 3/2015 |
|---|---|---|
| EP | 2845541 A1 | 3/2015 |
| WO | WO 2012/156886 A1 | 11/2012 |

OTHER PUBLICATIONS

Goli et al., "Graphene-enhanced hybrid phase change materials for thermal management of Li-ion batteries" Journal of Power Sources vol. 248, Feb. 2014, p. 248 37-43 (available online Sep. 24, 2013) (Year: 2013).*

(Continued)

*Primary Examiner* — Colin T. Sakamoto
(74) *Attorney, Agent, or Firm* — Dickinson Wright PLLC

(57) ABSTRACT

An ultrasound probe comprising a housing, a transducer assembly operable to transmit ultrasonic energy towards a zone of the probe adapted to be acoustically coupled to an object or area of interest, a cooling system comprising a heat transfer device arranged to transfer heat generated by the transducer assembly to one or more regions or areas located outside such transducer assembly. The heat transfer device comprises graphene.

8 Claims, 5 Drawing Sheets

(52) U.S. Cl.
CPC ............... *A61B 8/546* (2013.01); *A61N 7/00* (2013.01); *G10K 11/02* (2013.01)

(56) References Cited

U.S. PATENT DOCUMENTS

| | | | |
|---|---|---|---|
| 5,555,887 A | 9/1996 | Fraser | |
| 5,560,362 A * | 10/1996 | Sliwa, Jr. | G10K 11/004 |
| | | | 600/459 |
| 5,634,466 A | 6/1997 | Gruner | |
| 5,721,463 A | 2/1998 | Snyder | |
| 6,663,578 B1 * | 12/2003 | Peszynski | A61B 8/467 |
| | | | 601/2 |
| 6,669,638 B1 * | 12/2003 | Miller | A61B 8/546 |
| | | | 600/438 |
| 7,052,463 B2 | 5/2006 | Peszynski et al. | |
| 7,105,986 B2 | 9/2006 | Wildes et al. | |
| 7,308,828 B2 | 12/2007 | Hashimoto | |
| 7,694,406 B2 | 4/2010 | Wildes et al. | |
| 8,377,408 B2 | 2/2013 | Dickinson, III et al. | |
| 9,186,123 B1 * | 11/2015 | Dunham | G10K 11/004 |
| 2004/0002655 A1 * | 1/2004 | Bolorforosh | B06B 1/06 |
| | | | 600/459 |
| 2004/0073113 A1 * | 4/2004 | Salgo | A61B 8/00 |
| | | | 600/438 |
| 2005/0075573 A1 * | 4/2005 | Park | A61B 8/12 |
| | | | 600/459 |
| 2005/0215892 A1 * | 9/2005 | Emery | A61B 8/546 |
| | | | 600/459 |
| 2006/0191344 A1 * | 8/2006 | Hashimoto | A61B 8/546 |
| | | | 73/632 |
| 2007/0015112 A1 * | 1/2007 | Hochman | A61B 8/546 |
| | | | 433/215 |
| 2008/0200845 A1 * | 8/2008 | Sokka | A61K 41/0033 |
| | | | 601/3 |
| 2008/0214938 A1 * | 9/2008 | Solomon | G01S 7/5205 |
| | | | 600/459 |
| 2010/0016727 A1 | 1/2010 | Rosenberg | |
| 2010/0085713 A1 | 4/2010 | Balandin et al. | |
| 2012/0007471 A1 | 1/2012 | Tai | |
| 2012/0060610 A1 * | 3/2012 | Oaks | A61B 8/4444 |
| | | | 73/632 |
| 2012/0116228 A1 | 5/2012 | Okubo | |
| 2012/0238880 A1 | 9/2012 | Davidsen | |
| 2013/0303918 A1 * | 11/2013 | Miyajima | A61B 8/4444 |
| | | | 600/459 |
| 2013/0345567 A1 | 12/2013 | Sudol | |
| 2014/0003822 A1 | 1/2014 | Calabro | |
| 2014/0033822 A1 | 2/2014 | Yoon et al. | |
| 2014/0360274 A1 * | 12/2014 | Cho | G01N 29/0654 |
| | | | 73/644 |
| 2014/0364742 A1 * | 12/2014 | Cho | A61B 8/4444 |
| | | | 600/459 |
| 2015/0065883 A1 | 3/2015 | Lee | |
| 2015/0289850 A1 * | 10/2015 | Lewis | A61B 8/546 |
| | | | 600/459 |
| 2015/0289854 A1 * | 10/2015 | Cho | H05K 1/0204 |
| | | | 600/463 |
| 2016/0041129 A1 * | 2/2016 | Cho | A61B 8/4444 |
| | | | 73/643 |

OTHER PUBLICATIONS

Zalba, Belen et al., "Review on Thermal Energy Storage with Phase Change: Materials, Heat Transfer Analysis and Applications", Applied Thermal Engineering, Pergamon, Oxford, GB, vol. 23, No. 3, Feb. 1, 2003 (Feb. 1, 2003), pp. 251-283, XP008149082.
"Scientific Background on the Nobel Prize in Physics 2010, Graphene", The Royal Swedish Academy of Sciences, Oct. 5, 2010, 10 pages.
Kenisarin, Murat et al., "Solar Energy Storage Using Phase Change Materials", Renewable & Sustainable Energy Reviews, RSER—Nov. 9, 2007, www.elsevier.com/locate/rser, 53 pages.
Fuchs, Jean-Noël et al., "Introduction to the Physical Properties of Graphene", Lecture Notes 2008, http://users.lps.u-psud.fr/GOERBIG/CoursGraphene2008.pdf. 65 pages.
Sharma, Atul et al., "Review on Thermal Energy Storage with Phase Change Materials and Applications", Renewable & Sustainable Energy Reviews, RSER 13 (2009) www.elsevier.com/locate/rser, pp. 318-345.
Novoselov, K.S. et al., "Electric Field Effect in Atomically Thin Carbon Films", Science, Oct. 22, 2004, 5 pages.
Anonymous: "List of Thermal Conductivities—Wikipedia, the Free Encyclopedia", Dec. 29, 2013 (Dec. 29, 2013), XP055219638, Retrieved from the Internet: URL:https://en.wikipedia.org/w/index.php?title=List_of_thermal_conductivities&oldid=588284515.
(Review on thermal energy storage with phase change materials, heat transfer analysis and Application's applied thermal Engineering 23;2003 251-283).

* cited by examiner

ULTRASOUND PROBE WITH OPTIMIZED THERMAL MANAGEMENT

This application is a continuation of U.S. patent application Ser. No. 15/126,656, filed Sep. 16, 2016, which is based on PCT Application No. PCT/EP2015/067151, filed Jul. 27, 2015, which claims the benefit of European Patent Application No. EP14183233.7, filed Sep. 2, 2014, the entire contents of which are incorporated herein by reference.

FIELD OF THE INVENTION

The invention relates to the technical field of ultrasound probes, particularly in the medical field, although it can find applications also in the non-destructive testing field.

STATE OF THE ART

Ultrasound diagnostic technology generally relates to imaging of biological tissue using an ultrasonic transducer probe. The probe includes a transducer which transmits ultrasonic waves and receives ultrasonic echoes reflected from the tissue. The transducer is typically placed on the body surface or internal to a body lumen of a patient in a selected imaging region. The ultrasound transducer generates and directs ultrasonic waves to the imaging region. The transducer then receives ultrasonic waves reflected from the region and converts the received waves into electrical signals that are processed to form a diagnostic image.

In the case of ultrasound treatment, high-intensity focused ultrasound energy is applied to locally heat and destroy diseased or damaged tissue. An example is HIFU (High-Intensity Focused Ultrasound), a class of clinical therapies that uses ultrasound-induced hyperthermia to treat diseases. Another application is lithotripsy where acoustic energy is used to destroy stones, typically kidney stones.

In both imaging and therapy applications, an undesirable thermal build-up is created in the probe during transmission due to acoustic losses being converted into heat. Prescribed limits are set or prescribed by governing agencies as to the amount of heat that can be allowed to build up on the surface of the probe, typically limiting the surface temperature of the probe tip to a predetermined temperature or to a predetermined increase above room temperature, and hence limiting the acoustic output. Optimal transducer performance is obtained when the surface temperature of the probe tip is maintained at a specified temperature, such as room temperature, regardless of the acoustic output.

Various methods have been proposed for thermal management in ultrasonic probes. Conventional methods prescribe passive cooling of the transducer structure by transferring heat from the source into the body and handle of the probe.

U.S. Pat. No. 5,545,942 proposes the use of heat conductors to be placed around the periphery of the transducer package, but within the probe housing, so that heat can be drawn away from the transducer face and toward the rear/interior of the probe. The heat conductors act as conduits for draining away heat which builds up in the thermal potting material during pulsation of the piezoelectric transducer elements. The heat conductors are formed from metal foil, typically aluminium, having a heat conductivity greater than the heat conductivity of the thermal potting material which fills the spaces inside the probe housing and surrounds the transducer package.

U.S. Pat. No. 5,721,463 teaches how to use the cable components as heat conductors which conduct heat out of the probe handle. These heat pipes are coupled to an internal heat conductor which is in heat conductive relationship with the transducer pallet. Thus, heat generated by the transducer array can be transferred, via the internal heat conductor plate and the cable heat conductors, away from the probe surface which contacts the patient. Alternatively, inlet and return flow paths for cooling fluid are incorporated in the cable. The inlet and return flow paths inside the cable are respectively connected to the inlet and outlet of a flow path which is in heat conductive relationship with an internal heat conductor in the probe handle.

In WO 2012156886 the heat developed in the transducer stack is coupled to a metallic frame inside the handle of probe. A metallic heatspreader is thermally coupled to the probe frame to convey heat away from the frame. The heatspreader surrounds the inside of the probe handle and has an outer surface which is thermally coupled to the inner surface of the probe housing. Heat is thereby coupled evenly from the heatspreader into the housing without the development of hotspots in the housing which could be uncomfortable to the hand of the sonographer.

U.S. Pat. Nos. 7,105,986 and 7,694,406 disclose a composite structure of a backing material with enhanced conductivity for use in a transducer. The composite structure includes a plurality of layers of backing material alternatingly arranged with a plurality of thermal conductive elements, wherein the plurality of thermal conductive elements are configured to transfer heat from a center of the transducer to a plurality of points on the composite structure of backing material.

U.S. Pat. No. 5,560,362 teaches active cooling by using an open loop cooling system, a closed loop circulating cooling system, a thermoelectric cooling system and an evaporator/condenser system. U.S. Pat. No. 5,961,465 teaches transferring of heat from integrated circuits located within the housing of the probe and approximating the transducer, where the transfer of heat is provided by a circulating cooling system.

The above methods transfer heat away from, or cool, the portion of the transducer structure that is internal to the probe, and therefore remote from the biological tissue being imaged. However, the primary source of heat generation is the area of the probe closest to the biological tissue, namely, the area of the transducer from which the acoustic energy is transmitted towards the biological tissue, and the adjacent lens in contact with the biological tissue through which the acoustic energy is focused and directed into the biological tissue.

U.S. Pat. No. 7,052,463 discloses an active cooling system which includes a conduit for circulating cooling medium and a heat exchanger in fluid communication with the circulating cooling medium and having means for removing heat from the circulating cooling medium, wherein at least a portion the conduit is in proximity to or contacts the outer surface of the probe tip.

Although efficient, this system requires an active device external to the transducer which renders the probe cumbersome and rather complicated, particularly with reference to passive cooling approach.

A first attempt to drain heat passively from the tip of the probe can be found in the already mentioned U.S. Pat. No. 5,721,463. This document, among various embodiments, teaches a thermal enhancement layer consisting of a film of diamond or diamond-like carbon-based material, which is highly thermally conductive, formed on the acoustic components at the distal end of the probe.

In U.S. Pat. No. 5,402,793 and U.S. Pat. Appl. published with number 2010/016727 usage of graphite is envisioned.

These solutions go in the right direction, however, diamond has poor acoustic properties. An acceptable acoustic coupling would thus require an extremely thin film, which limits its ability to work as a heat drain device. Furthermore, a limit exists in the minimal achievable thickness of the layer due to the typical tri-dimensional structure of diamond that renders this solution impracticable. The same applies also to graphite although carbon in this material has a different ibridation that leads to a more planar structure. Thus, a need continues to exist for transferring heat from the tip of an ultrasound probe for providing improved acoustic and thermal coupling.

SUMMARY OF THE INVENTION

It is thus an object of the present invention to provide a handy and highly manoeuvrable probe having an optimized thermal management.

The invention reaches the aim with an ultrasound probe comprising:
a) a housing;
b) a transducer assembly operable to transmit ultrasonic energy towards a zone of the probe adapted to be acoustically coupled to an object or area of interest;
c) a cooling system comprising a heat transfer device arranged to transfer heat generated by the transducer assembly to one or more regions or areas located outside such transducer assembly, wherein such heat transfer device comprises a graphene-based material, particularly pure graphene or graphene charged with other components, for example resins to obtain a composite.

Graphene is a two-dimensional crystalline carbon-based material. It has been studied theoretically in 1947 by P. R. Wallace—Physical Review 71, 476 (1947), but it is only with the publication in October 2004 in Science 306, 666 (2004) by K. S. Novoselov, A. K. Geim et al. that this fascinating material began to stimulate an enormous scientific interest.

As extensively pointed out in the publication "Scientific Background on the Nobel Prize in Physics 2010" compiled by the Class for Physics of the Royal Swedish Academy of Sciences, 5 Oct. 2010, graphene has a number of properties which makes it interesting for several different applications. It is an ultimately thin, mechanically very strong, optical transparent and flexible conductor. Its conductivity can be modified over a large range either by chemical doping or by an electrical field. The mobility of graphene is very high which makes the material very interesting for electronic high frequency applications. Recently it has become possible to fabricate large sheets of graphene. Using near-industrial methods, sheets with width of 70 cm have been produced. Since graphene is a transparent conductor, it can be used in applications such as touch screens, light panels and solar cells, where it can replace the rather fragile and expensive Indium-Tin-Oxide (ITO). Flexible electronics and gas sensors are other potential applications. The quantum Hall effect in graphene could also possibly contribute to an even more accurate resistance standard in metrology. New types of composite materials based on graphene with great strength and low weight could also become interesting for use in satellites and aircrafts.

The inventors, knowing the properties of graphene in terms of enhanced thermal conductivity, began considering this material while studying possible solutions to the problem of thermal management of ultrasound probes. After the first tests, it came to their surprise that this material revealed not only a very good thermal conductivity, but also a very low acoustic impedance. Particularly such acoustic impedance is close enough to that of silicone rubber commonly used as last stage of a transducer assembly acting as acoustic lens to be placed in contact with skin. This would allow to place graphene almost on the top of the transducer assembly without affecting significantly the whole acoustic coupling of the probe.

Furthermore, due to its high strength, graphene seems to act as a good chemical barrier to alcohol with results comparable to Kapton so that placing a layer of this material in the transducer assembly would bring also this additional benefit.

To such extent, according to an embodiment, the transducer assembly comprises one or more transducer elements operable to generate ultrasound waves with the heat transfer device comprising one or more layers of the graphene-based material placed between such transducer elements and the coupling zone of the probe. Particularly, as the transducer assembly typically comprises one or more acoustic matching layers, the graphene-based material can be arranged to form a heat transfer layer placed in the transducer assembly as a substitute of at least one of such matching layers or in addition to them.

According to a preferred solution, the heat transfer layer is the furthest from the transducers elements towards the coupling zone of the probe due to its very low acoustic impedance. The heat transfer layer can be considered a matching layer hence its thickness is advantageously chosen to be not greater than a ¼ of the wavelength of the ultrasound waves the probe is configured to generate.

The graphene-based material may be pure graphene or a composite, for example obtained from graphene and epoxy resin. In this case, it is preferably in the form of stripes of graphene interleaved with stripes of resin or a layer of graphene with holes filled with resin to realize a more mechanically stable structure. Graphene, in fact, tends to exfoliate and providing it with holes or slots for a resin to grab can allow to realize a more reliable compound.

According to an embodiment, the cooling system comprises a heat dissipating and/or storing device located in the housing in thermal communication with the heat transfer device. The heat dissipating and/or storing device is preferably in thermal communication with the heat transfer layer via a heat transfer circuit comprising a conductive material, typically formed of the same graphene-based material. The heat transfer device is, for example, a layer of graphene located between the transducer elements and the coupling zone of the probe and peripherally bended to form a longitudinal path extending laterally from the front to the rear of the probe.

A heat dissipating device can be, for example, the typical metallic block supporting the backing or any other metallic part within the probe case or the attached cable while a heat storing device can advantageously be any thermostating system able to absorb heat maintaining the temperature constant as, for example, those based on PCM (Phase Change Materials).

According to an improvement, the backing element, located on the rear side of transducer elements opposite to the emitting surface, is charged with graphene to improve its thermal conduction. This because the inventors found that also the acoustic properties of graphene in terms of dumping of undesired oscillations are surprisingly good. The backing material rendered thermally conductive by charging it with graphene can obviously exist independently from the layer of graphene placed in the frontal part of the probe.

According to an embodiment, the transducer assembly comprises matching/heat transfer layers located between the frontal emitting surface and the coupling zone of the probe and a backing element located on the rear side of transducer elements opposite to the emitting surface, with a heat dissipating material located between the backing element and the housing opposite to the coupling zone of the probe to receive heat from the heat transfer layer and/or the backing element.

The heat storing device, which may substitute, at least partially, or be in addition to the heat dissipating device, typically comprises a Phase Changing Material (PCM) that acts as a thermostating element able to absorb heat typically maintaining the temperature constant. The PCM is preferably an organic reversible transition material that stores heat in the form of latent heat while changing phase from solid to liquid and releases stored heat when changing phase from liquid to solid.

The heat storage device may advantageously comprise graphene and more specifically a composite material including a PCM and a filler charged with graphene. The filler is typically a resin, such as an epoxy resin, charged with graphene with the PCM being micro-encapsulated by such graphene-charged resin.

The heat storing device is advantageously arranged to fill available spaces inside the probe housing to temporarily store heat drained away from the transducer assembly. It can obviously be located also outside the housing, for example in the cable.

According to an embodiment, in an ultrasound probe having a probe housing that encloses a transducer assembly, a heat storing device is provided that is based on Phase Change Material (PCM) able to absorb heat maintaining the temperature constant, wherein the heat storing device comprises graphene and is disposed in an area within the probe housing.

The heat storing device may advantageously comprise a composite material including a PCM and a filler charged with graphene.

The filler may advantageously be a resin, such as an epoxy resin, charged with graphene, the PCM being micro-encapsulated by such graphene-charged resin.

The heat storing device may advantageously be configured to be interspersed in the probe housing in any position and without specific sites or receptacles to host the composite material due its micro-encapsulation.

The heat storing device may advantageously be an organic reversible PCM that accumulates heat in the form of latent heat while changing phase from solid to liquid and releases accumulated heat when changing phase from liquid to solid.

The heat storing device may advantageously be disposed in a rear part of the probe housing.

The heat storing device may advantageously be a filling material disposed in a rear part of the probe housing.

The filling material may advantageously be arranged to fill available spaces inside the probe housing to temporarily store heat drained away from the transducer assembly.

According to an embodiment, in an ultrasound probe having a probe housing that encloses a transducer assembly, a heat storing device is provided that is based on Phase Change Material (PCM) able to absorb heat maintaining the temperature constant, wherein the heat storing device comprises graphene and is disposed wherein the heat storing device is disposed externally to the probe housing.

The heat storing device may advantageously be disposed relative to a cable connected to the probe housing.

The heat storing device may advantageously comprise a composite material including a PCM and a filler charged with graphene.

The filler may advantageously be a resin, such as an epoxy resin, charged with graphene, the PCM being micro-encapsulated by such graphene-charged resin.

Further improvements of the invention will form the subject of the dependent claims.

BRIEF DESCRIPTION OF THE DRAWINGS

The characteristics of the invention and the advantages derived therefrom will be more apparent from the following description of non-limiting embodiments, illustrated in the annexed drawings, in which.

DETAILED DESCRIPTION OF A PREFERRED EMBODIMENT

Figure 1:
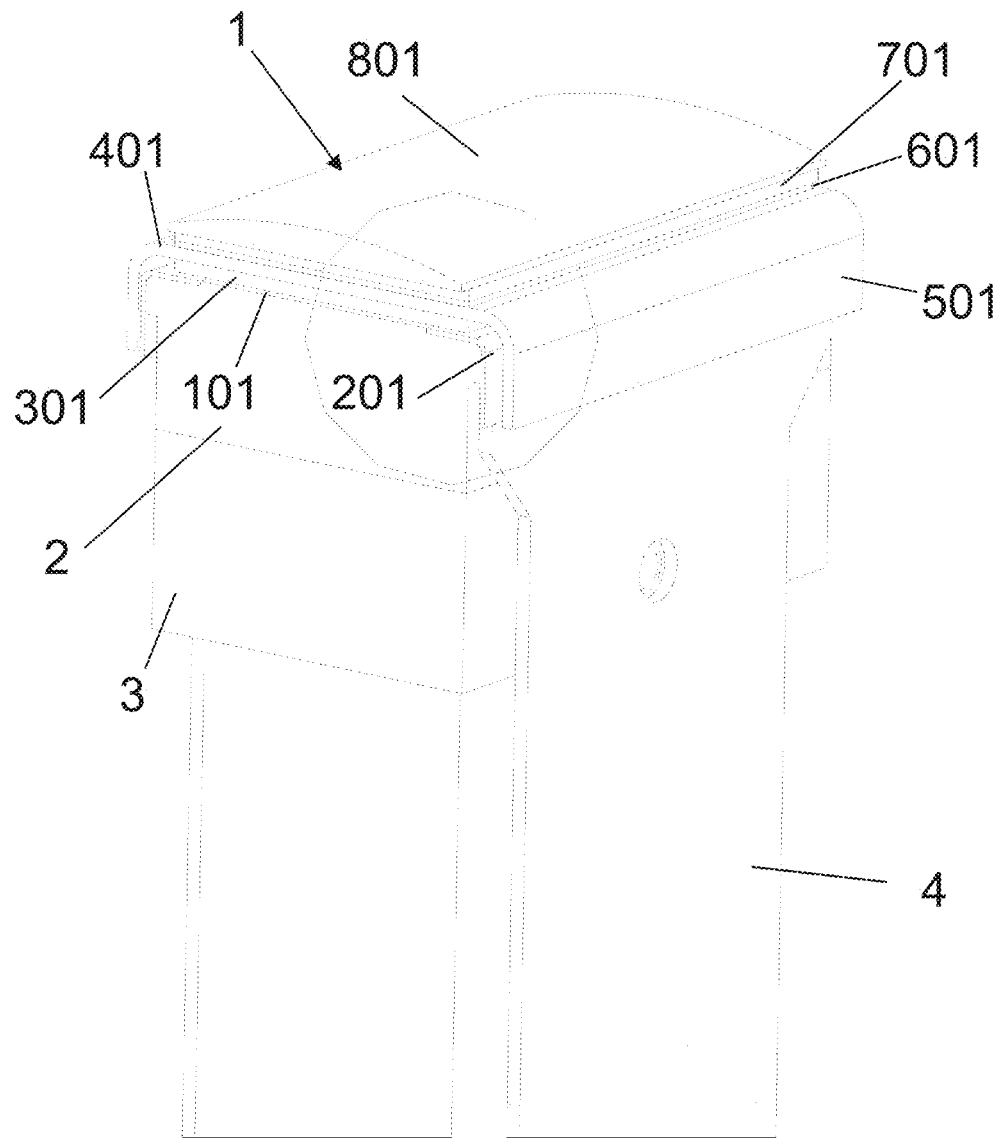
FIG. 1 shows a perspective view of a conventional probe according to the state of the art.
Figure 2:
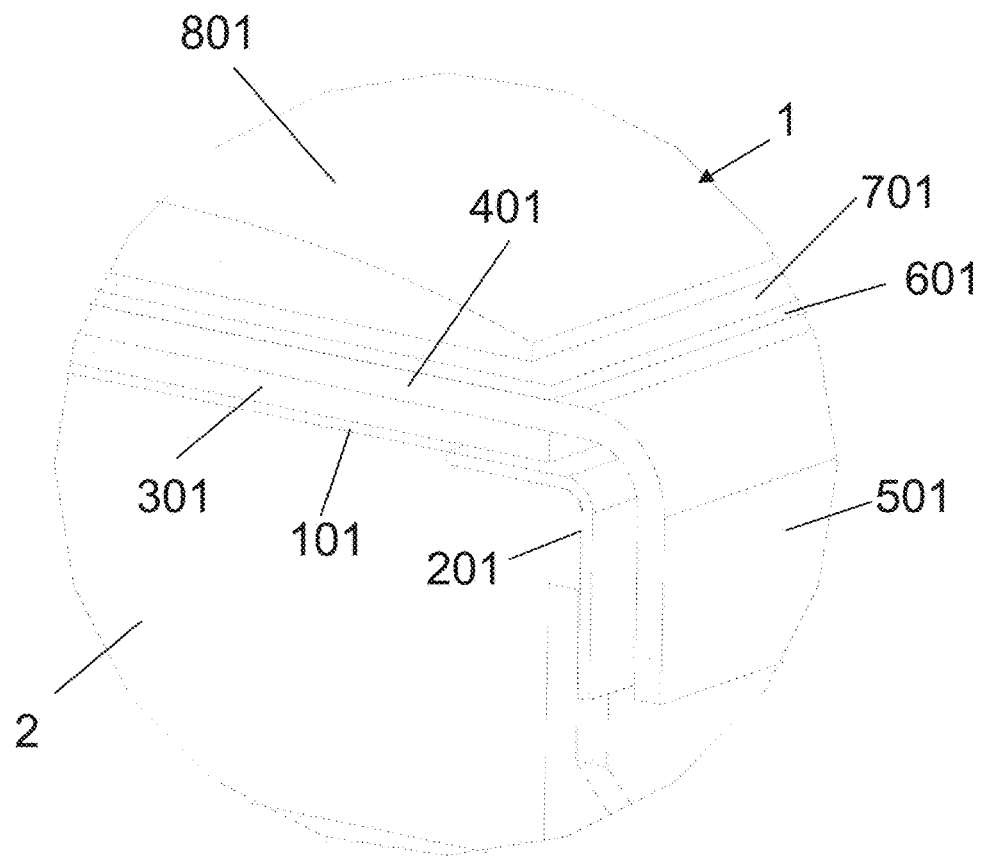
FIG. 2 shows an enlarged view of the head of the probe according to FIG. 1.
Figure 3:
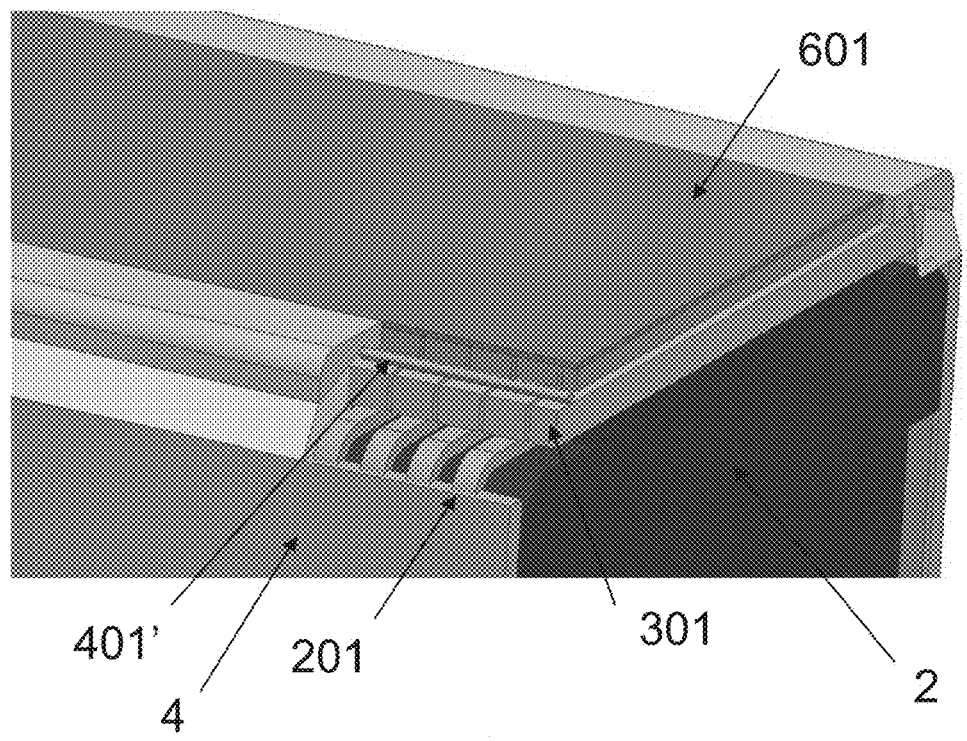
FIG. 3 schematically shows a probe head with ground wire connections arranged to contact transducer elements of a same raw.

Referring to FIGS. 1 to 3, a conventional probe is illustrated therein. The probe comprises an ultrasound waves emitting and receiving head 1 which has a front side from which the ultrasound waves are emitted in the direction against a target, such as a body under examination, and on which the reflected ultrasound waves or incoming ultrasound waves impinge and are sensed. The ultrasound head 1 has a back side 3 which is opposite to the said front side and which is oriented towards the inside of a probe casing and towards means for supporting the probe head provided inside the probe casing.

The probe head 1 comprises, in an order starting from the back side of the said head towards the front side of the said head, which order corresponds also to the direction of propagation of the emitted ultrasound waves, a first layer 101 formed by an array of contact electrodes. Each contact electrode of this layer 101 of contact electrodes has a separate electric connection line to a corresponding contact pin on a contact termination provided along at least one edge of the layer of contact electrodes and indicated with 201. The layer 101 of contact electrodes is typically in the form of an array of at least electrically separated contact electrodes since each one of the said contact electrodes has the function of feeding the electric excitation signal to the associated transducer and of collecting the electric receipt signal from the associated transducer when the said transducer is mechanically excited by an impinging ultrasound wave. Some electrodes could be short circuited as in 1,25D, 1.5D or 1.75D probes.

On the layer formed by the array of contact electrodes, an array of piezoelectric elements 301 is laid. Each one of the piezoelectric elements forms an emitting and receiving transducer. Piezoelectric elements are typically fabricated from lead zirconate titanate (PZT), PZT-resin composite or Single Crystal material. The single transducers are each one coincident and in electric contact with one of contact electrodes of the layer 101. In a possible configuration, a further layer of conductive material 401 is laid on the layer 301 formed by the array of transducers. The conductive material of the layer 401 is in electric contact with each one of the said piezoelectric elements and is connected to ground potential by means of a contact termination 501. The layer 401 of conductive material forms the ground electrode of the transducers of the layer 301. The layer 401 may be in the form of an array of ground electrodes, but since the ground potential is common to every of the transducers of the layer 301 there is no need to provide separate ground electrodes for each transducer, so that the said layer 401 can be easily formed by a continuous layer of conductive material. Alternatively, the ground connections may be formed by a microscopic section wire 401' contacting elements belonging to a same raw as shown in FIG. 3. On the array of piezoelectric material elements 301 matching layers are provided which are indicated with numerals 601 and 701 in FIGS. 1 and 2. These layers (two in the example of FIG. 2, one in FIG. 3) have the function of adapting the acoustic impedance of the piezoelectric elements to the acoustic impedance of the target. Normally two or three layers are used in order to provide a progressive stepwise adaptation which also allows to maintain a sufficiently large bandwidth for the passing ultrasound waves. In each material the acoustic impedance is given by the product of density times speed of sound and can be considered equivalent to the electrical impedance for an electrical circuit with many power transfer stages. The thickness of each matching layer generally follows the $\lambda/4$ rule, so they depend on their operating frequency (generally from 2 MHz to 12 MHz for standard imaging probes) and speed of sound in each material. Matching layer are generally manufactured from epoxy resin loaded with metallic powder. In the configuration with grounded conductive layer 401 (see FIGS. 1 and 2) the first matching layer 601 is generally placed above such grounded layer 401. In case of wiring connection 401' as in FIG. 3, the first matching layer 601 is in direct contact with the piezoelectric elements 301.

Typically the first matching layer 601 is made of a material having an acoustic impedance of about 5 to 12 MRayl and the last matching layer 701 has an acoustic impedance of about 2 MRayl.

As a last element, on the matching layer 701, an acoustic lens 801, typically of silicone rubber, is placed which forms the interface between the head of the probe 1 and the surface of a target body. The aim of such a lent is to focus the ultrasound beam in the elevation plane.

The contact terminations 201 and 501 of the layer 101 formed by the array of contact electrodes and of the layer 401 or wires 401' formed by the grounded conductive material are electrically and mechanically connected to a printed circuit board 4 which provides the necessary conductive tracks which are connected to a probe connection cable (not shown) via connector 8 and which cable connects the probe with an ultrasound apparatus as for example an ultrasound imaging apparatus.

The probe head 1 is generally stuck on a backing material 2 that acts both as a support and as a damping device for the back-travelling acoustic wave, to minimize reverberations and ringiness. Backing material is generally a special hard rubber compound with poor thermal conductivity. A metallic, typically aluminium, block 3 acts as a support for the backing material 2. Where the term "backing" occurs it is understood as meaning a solid mass, of suitable geometry, on which the piezoelectric elements are mounted; when this component is excited by a voltage pulse, the oscillation is dampened and the reduction in the amplitude between successive oscillations depends on the material with which the component is combined. This base must therefore have particular acoustic properties in terms of impedance and absorption in order to obtain the desired level of attenuation.

Getting into the heat generation process, during use, the system connected to the probe transmits an electrical signal through the connectors and cable to the acoustic stack. The piezoelements 301 convert the electrical signal into acoustic output energy emitting from the silicone rubber lens 801 into the target under examination. During reception of the echo acoustic signal, the piezoelements 301 sense the electrical disturbance produced by acoustic energy bounced off of the target (internal patient tissue in case of a diagnostic device) and reflected back into the transducer. It's mainly the transmit portion of the process that is responsible of heat generation. This is because the electroacoustic energy conversion process is less than 100% efficient. Thus the piezoelements act as unintended heaters. Moreover, as ultrasound energy is produced by the piezoelements, it is partially absorbed by matching layers 601, 701, lens 801 and backing 2, all usually not being totally lossless. Thus heat is generated both in the piezoelements 301 and in the other materials of the probe head 1.

Figure 4:
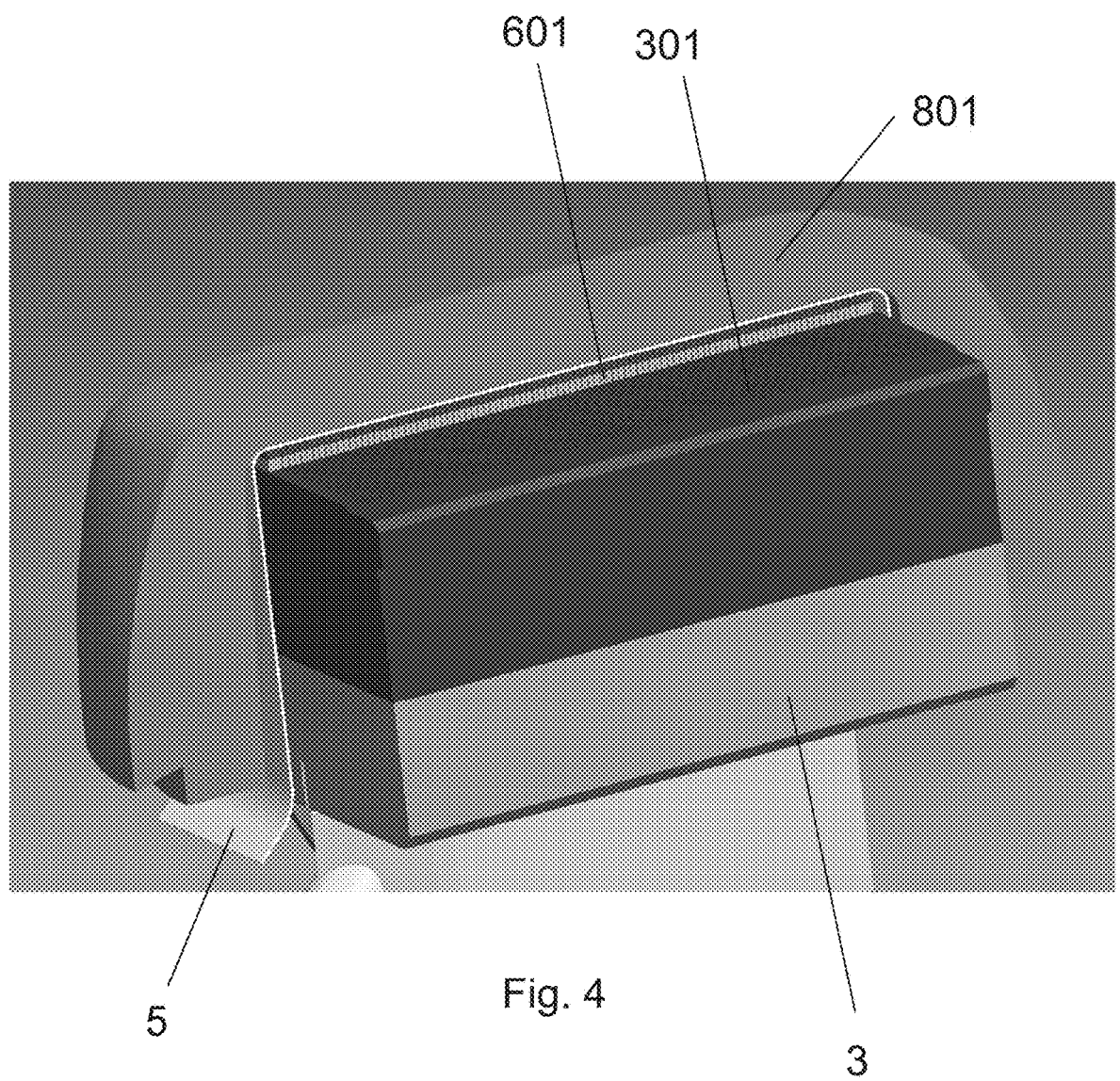
FIG. 4 schematically shows a probe head according to the invention.
Figure 7:
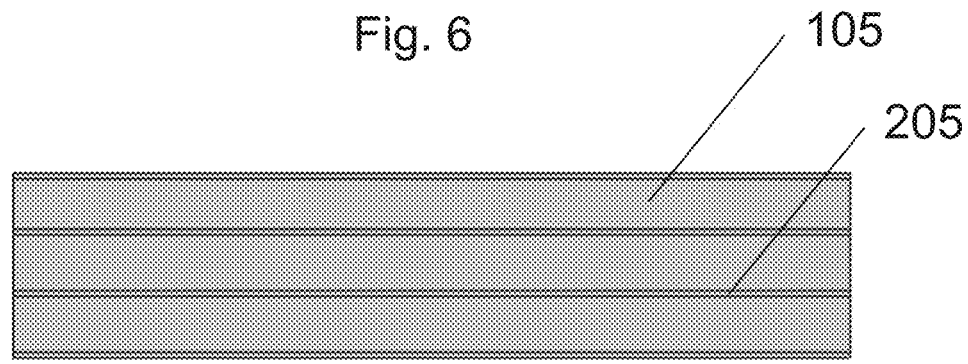
FIGS. 7 and 8 show structures of graphene suitable to be used in the present invention.
Figure 8:
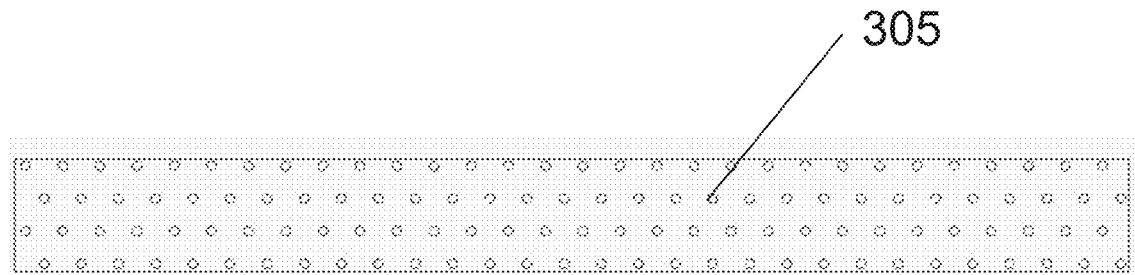

According to a first embodiment of the invention, heat is drained away using a layer 5 of graphene, or, more generically, of a compound comprising graphene, that is placed in front of the last matching layer 601 just before the acoustic lens 801 as exemplary shown in FIG. 4. The graphene compound may be simply one or more sheet of graphene or a more complex compound such as a layer of a composite obtained from graphene and resin such as an epoxy resin. Referring to FIG. 7, the compound may consist in stripes of graphene 105 besides epoxy ones 205. The width values are, for example, 1 mm and 0.1 mm respectively, with thickness varying with dependence on probe frequency according to the so-called $\lambda/4$ rule as if it were a matching layer. The structure can be manufactured by a standard bond-dice-fill procedure, similar to the one used for probe array manufacturing, or it can be developed during the graphene layer synthesizing process. Another example is shown in FIG. 8. In this case the layer of graphene has holes 305 where resin can rest to realize a more mechanically stable structure. Graphene, in fact, tends to exfoliate and providing it with holes or slots for a resin to grab can allow to realize a more reliable compound.

The layer of graphene or graphene-based compound can be placed in any position starting from the transducer array 301, for example before the first matching layer 601 or after that, before or after the second matching layer 701. The acoustic impedance of the graphene-compound was measured and found to be surprisingly low, close to the value for silicone rubber, within experimental measurement approximation. Such property allows to use graphene, in a particularly advantageous embodiment, between the piezoelectric array 301 and the silicone lens 801 with negligible probe performance loss.

Alternatively or in combination heat can also be transferred by charging backing 2 with graphene thus rendering the same thermally conductive.

Figure 5:
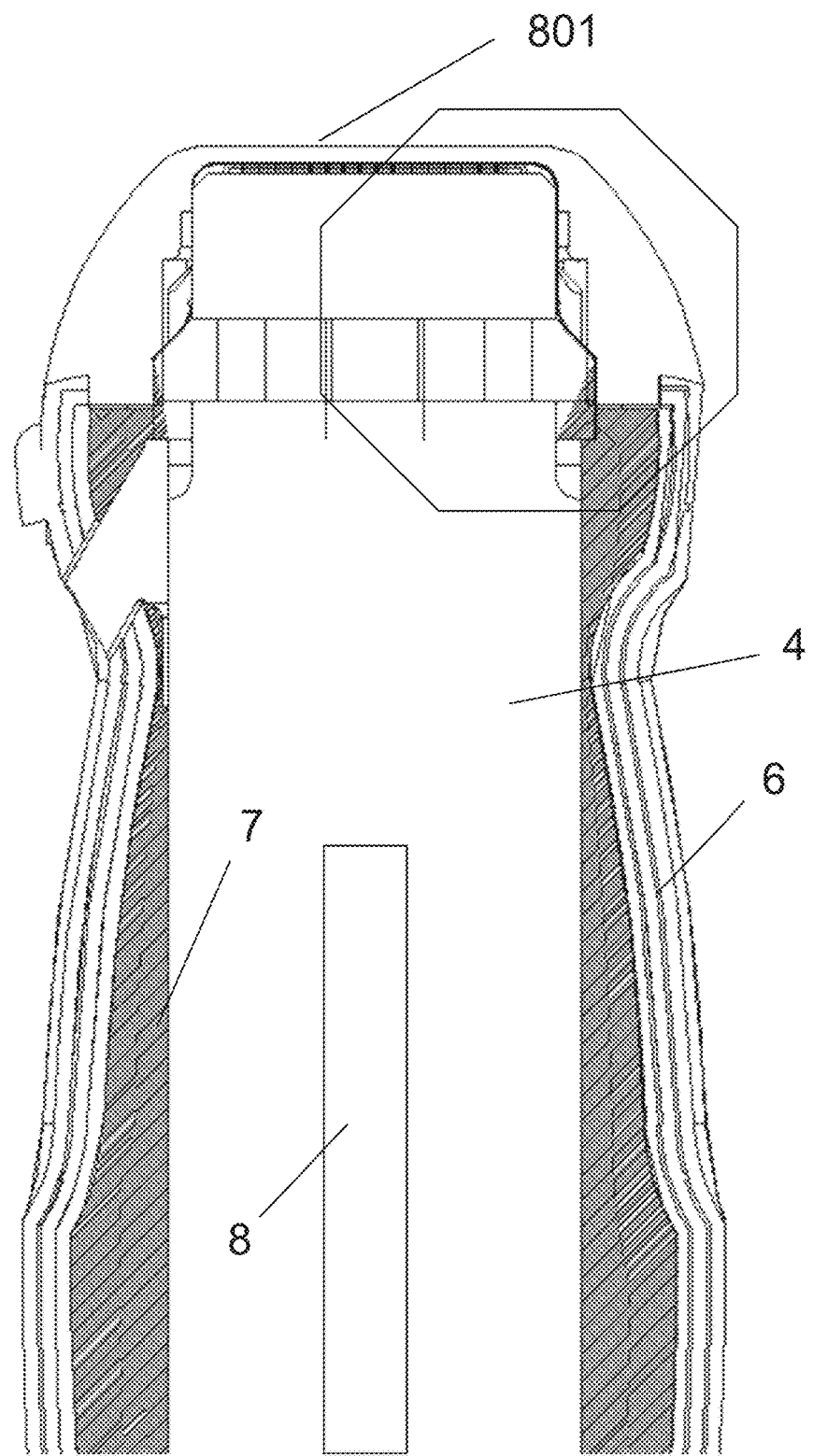
FIG. 5 shows a sectional view of a probe according to an embodiment of the invention.
Figure 6:
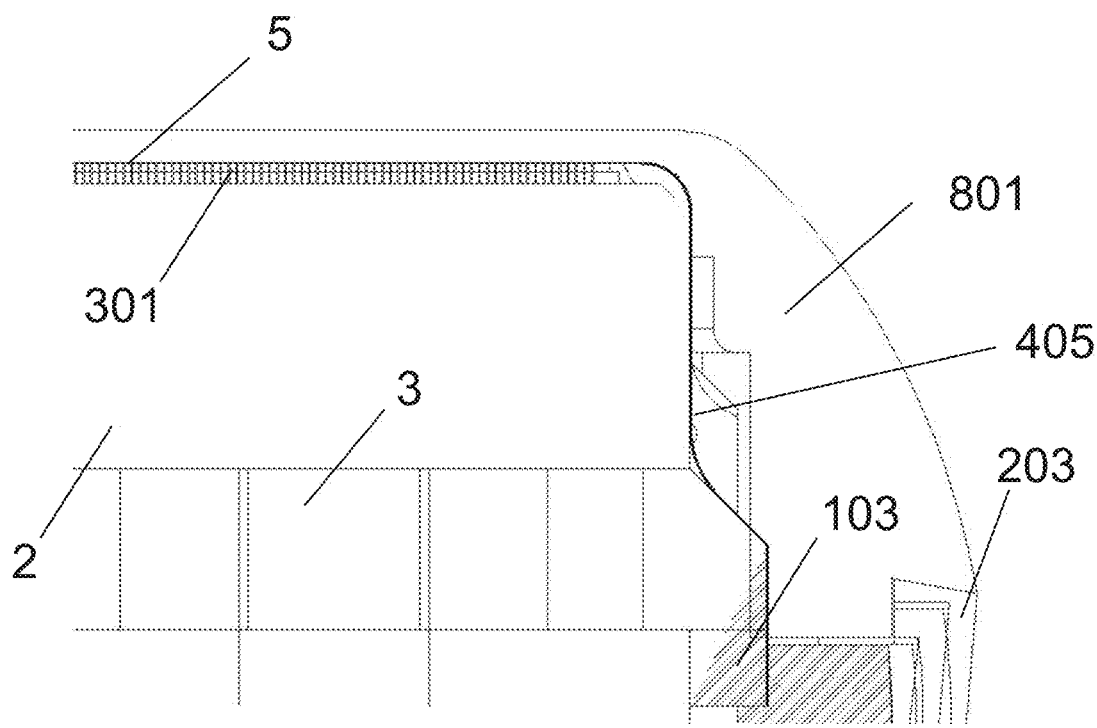
FIG. 6 shows an enlarged view of the head of the probe according to FIG. 5.

In FIG. 5 a probe according to the invention is illustrated. The layer of graphene-based material 5 is positioned below the acoustic silicone lens 2 of a common probe, then folding and extending to the rear part of the transducer stack. The thickness was chosen to be corresponding or less than the A/4 value for its sound speed in agreement with the acoustic design. The layer 5 laterally extends between the backing material 2 and the silicone lens 801 to reach the metal, typically aluminium, block 3 where the heat is conveyed. Alternatively or in combination, the thermal path 405 realized by the layer 5 is closed on a zone 103 located between the probe head 1 and the external ergonomic case 6. This zone 103 may be located directly in contact with the aluminium block 3 or in any area of the case 6 located in the rear part of the probe, i.e. on the opposite side with reference to the acoustic lens 801, to act as a heat sink. Also backing 2 can act as heat drain if rendered thermally conductive by charging it with graphene. Due to its position, in this case heat finds a preferential path to the aluminium block 3.

Backing charged with graphene in combination with a layer of graphene acting as heat drain from the front part of the probe provides the preferred solution to the problem of thermal management of ultrasound probes, although both solutions (graphene layer and graphene-charged backing) can find independent application.

The heat sink 103 may be thermally connected to the probe case 6 by a thermally conductive filler 6, so that the ability of the probe to spread heat to the environment is governed primarily by passive free convection of heat from the external surfaces of the probes. Of course there is a limit in the capacity to remove heat by natural convection of air from the external probe surface, that depends by the efficiency of the designed thermal path and the span of dissipation effective surface area. An improvement may consist in spreading some of the heat down the length of the attached cable in order to extend the passive convection surface area.

A better option is to consider an internal filling material 6 that may act as a heat storage device, subtracting heat at a fixed temperature by means of a phase transition process. Such material can be a Phase Changing Material (PCM) compound, with upgraded thermal properties.

The usage of a PCM in an ultrasound probe is known, for example, from U.S. Pat. No. 7,308,828, although not in combination with graphene-compounds acting as high efficiency thermal circuit. Example of PCMs can be found in Kenisarin, M. Mahkamov, K (2007), "Solar energy storage using phase change materials", Renewable and Sustainable Energy Reviews 11 (9): 1913-1965 and Sharma, Atul; Tyagi, V. V.; Chen, C. R.; Buddhi, D. (2009), "Review on thermal energy storage with phase change materials and applications", Renewable and Sustainable Energy Reviews 13 (2): 318-345 to be considered herein incorporated by reference.

PCMs may be classified in the following main categories:
organic such as paraffins ($C_nH_{2n+2}$) and fatty acids ($CH_3(CH_2)_{2n}COOH$),
inorganic such as salt hydrate ($M_nH_2O$);
eutectics such as lauric and stearic acids;
Hygroscopic materials Many types of PCM were studied by the inventors, in terms of transition temperature and latent heat/mass, but also in terms of other important features such as phase change efficiency of reversibility and interactions within a special compound. After several tests, organic, reversible PCMs were found to be the most suitable for the present application for the following properties:
Freeze without much supercooling;
Ability to melt congruently;
Self nucleating properties;
Compatibility with conventional material of construction;
No segregation;
Chemically stable;
High heat of fusion;
Safe and non-reactive;
Recyclable.

One of the tested organic PCMs has, for example, the following properties:
Transition Temperature: 27-35° C.
Latent heat: 155-175 J/Kg The working mechanism of a PCM is simple and mainly related to the physical characteristics of a substance to change status keeping the temperature constant until an amount of heat equal to the latent heat of the substance itself is exchanged. It is thus possible to use a PCM to accumulate an excess of heat simply letting it work in range of temperatures proximal to fusion or solidification. This, however, means that an appropriate receptacle is needed to contain the PCM when in a non solid state which would render its usage unhandy and rather complicated. A solution to this problem is a thermal-composite based on PCM, preferably of the organic type. Thermal-composite is a term given to combinations of phase change materials (PCMs) and other (usually solid) structures. A simple example is a copper-mesh immersed in a paraffin-wax. The copper-mesh within paraffin-wax can be considered a thermal-composite material.

By using a filler, such as epoxy resin, polyurethane, silicon or the like, to bind the PCM, it is possible to avoid its dispersion when in liquid state without the need to use specific containers.

The inventors found, however, that PCM materials can interfere with the process of polymerization of the filler with the result that the PCM is not strictly bound and remain highly movable in the composite. Furthermore fillers, particularly epoxy resins, are typically not thermally conductive with the result that, although the heat transfer circuit is highly efficient due to the presence of graphene acting as heat sink, the heat converter device based on PCM is not as efficient.

According to an improvement, the invention thus provides for a new category of PCM composites to be used as heat storing device, particularly in an ultrasound probe. These composites can be based on a highly thermally conductive resin or by the usage of a filler which is rendered by charging it with graphene. In this way a new PCM compound can be realized which is highly efficient and can be dispersed in any void space 7 available in the probe, particularly in the rear part of it.

To summarize, graphene is a very special substance that can be useful for thermal management of ultrasound probes. It can be used in the form of a matching layer to drain heat from the front of the probe or as filler of the backing to drain heat from the back of the probe. It can also find applications as a charging material of a filler encapsulating a PCM to be used as a heat converter to temporarily store heat in zones of the probes far from the front emitting surface. The heat converter can be interspersed in the probe in any position without having to provide specific sites or receptacles capable of hosting the material due to its microencapsulation in a binder. The usage of a thermal-composite including a PCM and graphene as heat sink has not to be strictly seen in combination with a heat drain according to the present invention, but can be an independent solution to the problem of a temporal heat storage device not only in the field of ultrasound probes, for example as alternative or improvement of the device disclosed in the already cited U.S. Pat.

No. 7,308,828, but also in any other field requiring an optimized thermal management.

Graphene is pure carbon in the form of a very thin, nearly transparent sheet, one atom thick. It is remarkably strong for its very low weight (100 times stronger than steel) and it conducts heat and electricity with great efficiency. While scientists had theorized about graphene for decades, it was first produced in the lab in 2004.

Technically, graphene is a crystalline allotrope of carbon with 2-dimensional properties. In graphene, carbon atoms are densely packed in a regular $sp^2$-bonded atomic-scale chicken wire (hexagonal) pattern. Graphene can be described as a one-atom thick layer of graphite. It is the basic structural element of other allotropes, including graphite, charcoal, carbon nanotubes and fullerenes. It can also be considered as an indefinitely large aromatic molecule, the limiting case of the family of flat polycyclic aromatic hydrocarbons.

Graphene is the only form of carbon (and generally all solid materials) in which each single atom is in exposure for chemical reaction from two sides (due to the 2D structure). It is known that carbon atoms at the edge of graphene sheets have special chemical reactivity, and graphene has the highest ratio of edgy carbons (in comparison with similar materials such as carbon nanotubes). In addition, various types of defects within the sheet, which are very common, increase the chemical reactivity. The onset temperature of reaction between the basal plane of single-layer graphene and oxygen gas is below 260° C. and the graphene burns at very low temperature (e.g., 350° C.). In fact, graphene is chemically the most reactive form of carbon, owing to the lateral availability of carbon atoms. Graphene is commonly modified with oxygen- and nitrogen-containing functional groups and analyzed by infrared spectroscopy and X-ray photoelectron spectroscopy.

Isolated 2D crystals cannot be grown via chemical synthesis beyond small sizes even in principle, because the rapid growth of phonon density with increasing lateral size forces 2D crystallites to bend into the third dimension. However, other routes to 2d materials exist:

Fundamental forces place seemingly insurmountable barriers in the way of creating 2D crystals. The nascent 2D crystallites try to minimize their surface energy and inevitably morph into one of the rich variety of stable 3D structures that occur in soot.

But there is a way around the problem. Interactions with 3D structures stabilize 2D crystals during growth. So one can make 2D crystals sandwiched between or placed on top of the atomic planes of a bulk crystal. In that respect, graphene already exists within graphite. One can then hope to fool Nature and extract single-atom-thick crystallites at a low enough temperature that they remain in the quenched state prescribed by the original higher-temperature 3D growth.

The two basic approaches to producing graphene are to cleave multi-layer graphite into single layers or to grow it epitaxially by depositing one layer of carbon onto another material. The former was developed first, using adhesive tape to peel monolayers away. In either case, the graphite must then be bonded to some substrate to retain its 2d shape. Other techniques have also been developed as reported below.

Exfoliation

As of 2014 exfoliation produced graphene with the lowest number of defects and highest electron mobility.

Adhesive Tape

Cleavage is also known as exfoliation. Achieving single layers typically requires multiple exfoliation steps, each producing a slice with fewer layers, until only one remains. Geim and Novosolev used adhesive tape to split their graphene.

After exfoliation the flakes are deposited on a silicon wafer using "dry deposition". Crystallites larger than 1 mm and visible to the naked eye can be obtained with the technique. It is often referred to as a "scotch tape" or "drawing" method. The latter name appeared because the dry deposition resembles drawing with a piece of graphite.

Wedge-Based Mechanical Exfoliation

Another controlled technique to produce few layers of graphene uses a wedge type of tool to address difficulties of the adhesive tape method. In this method, a sharp single-crystal diamond wedge penetrates onto the graphite source to exfoliate layers. This method uses highly ordered pyrolytic graphite (HOPG) as the starting material. The experiments were supported by molecular dynamic simulations.

Reduction of Graphite Oxide

Graphite oxide reduction was probably the first method of graphene synthesis. P. Boehm reported producing monolayer flakes of reduced graphene oxide in 1962. Geim acknowledged Boehm's contribution. Rapid heating of graphite oxide and exfoliation yields highly dispersed carbon powder with a few percent of graphene flakes. Reduction of graphite oxide monolayer films, e.g. by hydrazine with annealing in argon/hydrogen, was reported to yield graphene films. However, the quality is lower compared to scotch-tape graphene, due to incomplete removal of functional groups. Furthermore, the oxidation protocol introduces permanent defects due to over-oxidation. The oxidation protocol was enhanced to yield graphene oxide with an almost intact carbon framework that allows efficient removal of functional groups.

Sonication

Applying a layer of graphite oxide film to a DVD and burning it in a DVD writer produced a thin graphene film with high electrical conductivity (1738 siemens per meter) and specific surface area (1520 square meters per gram) that was highly resistant and malleable.

Solvent-Aided

Dispersing graphite in a proper liquid medium can produce graphene by sonication. Graphene is separated from graphite by centrifugation, producing graphene concentrations initially up to 0.01 mg/ml in N-methylpyrrolidone (NMP) and later to 2.1 mg/ml in NMP. Using a suitable ionic liquid as the dispersing liquid medium produced concentrations of 5.33 mg/ml. Graphene concentration produced by this method is very low, because nothing prevents the sheets from restacking due to van der Waals forces. The maximum concentrations achieved are the points at which the van der Waals forces overcome the interactive forces between the graphene sheets and the solvent molecules.

Solvent/Surfactant-Aided

Adding a surfactant to a solvent prior to sonication prevents restacking by adsorbing to the graphene's surface. This produces a higher graphene concentration, but removing the surfactant requires chemical treatments.

Immiscible Liquids

Sonicating graphite at the interface of two immiscible liquids, most notably heptane and water, producing macro-scale graphene films. The graphene sheets are adsorbed to the high energy interface between the heptane and the water, where they are kept from restacking. The graphene remains at the interface even when exposed to force in excess of 300,000 g. The solvents may then be evaporated. The sheets are up to ~95% transparent and conductive.

Epitaxy

Epitaxy refers to the deposition of a crystalline overlayer on a crystalline substrate, where there is registry between the two. In some cases epitaxial graphene layers are coupled to surfaces weakly enough (by Van der Waals forces) to retain the two dimensional electronic band structure of isolated graphene. An example of weakly coupled epitaxial graphene is the one grown on SiC.

Graphene monolayers grown on silicon carbide and iridium are weakly coupled to these substrates (how weakly remains debated) and the graphene-substrate interaction can be further passivated.

Silicon Carbide

Heating silicon carbide (SiC) to high temperatures (>1100° C.) under low pressures (~10-6 torr) reduces it to graphene. This process produces epitaxial graphene with dimensions dependent upon the size of the wafer. The face of the SiC used for graphene formation, silicon- or carbon-terminated, highly influences the thickness, mobility and carrier density of the resulting graphene.

Graphene's electronic band-structure (so-called Dirac cone structure) was first visualized in this material. Weak anti-localization is observed in this material, but not in exfoliated graphene produced by the drawing method. Large, temperature-independent mobilities approach those in exfoliated graphene placed on silicon oxide, but lower than mobilities in suspended graphene produced by the drawing method. Even without transfer, graphene on SiC exhibits massless Dirac fermions.

The weak van der Waals force that provides the cohesion of multilayer graphene stacks does not always affect the electronic properties of the individual layers. That is, while the electronic properties of certain multilayered epitaxial graphenes are identical to that of a single layer, in other cases the properties are affected, as they are in bulk graphite. This effect is well understood theoretically and is related to the symmetry of the interlayer interactions.

Epitaxial graphene on SiC can be patterned using standard microelectronics methods. A band gap can be created and tuned by laser irradiation.

Metal Substrates

The atomic structure of a metal substrate can seed the growth of graphene.

Ruthenium Graphene grown on ruthenium does not typically produce uniform layer thickness. Bonding between the bottom graphene layer and the substrate may affect layer properties.

Iridium

Graphene grown on iridium is very weakly bonded, uniform in thickness and can be highly ordered. As on many other substrates, graphene on iridium is slightly rippled. Due to the long-range order of these ripples, minigaps in the electronic band-structure (Dirac cone) become visible.

Nickel

High-quality sheets of few-layer graphene exceeding 1 cm² (0.2 sq in) in area have been synthesized via chemical vapor deposition on thin nickel films using multiple techniques.

The growth of graphene on nickle films through chemical vapor deposition occurs in a few steps. First the thin nickle film is exposed to Argon gas at 900-1000° Celsius. Methane is then mixed into the gas, and the carbon from the methane is absorbed into the nickel film. The nickle-carbon solution is then cooled down in argon gas. During the cooling process the carbon diffuses out of the nickle to form graphene films.

Another used temperatures compatible with conventional CMOS processing, using a nickel-based alloy with gold as catalyst. This process dissolves carbon atoms inside a transition metal melt at a certain temperature and then precipitates the dissolved carbon at lower temperatures as single layer graphene (SLG).

The metal is first melted in contact with a carbon source, possibly a graphite crucible inside which the melt is carried out or graphite powder/chunks that are placed in the melt. Keeping the melt in contact with the carbon at a specific temperature dissolves the carbon atoms, saturating the melt based on the metal-carbon binary phase diagram. Lowering the temperature decreases carbon's solubility and the excess carbon precipitates atop the melt. The floating layer can be either skimmed or frozen for later removal. Using different morphology, including thick graphite, few layer graphene (FLG) and SLG were observed on metal substrate. Raman spectroscopy proved that SLG had grown on nickel substrate. The SLG Raman spectrum featured no D and D' band, indicating its pristine nature. Since nickel is not Raman active, direct Raman spectroscopy of graphene layers on top of the nickel is achievable.

Another approach covered a sheet of silicon dioxide glass (the substrate) on one side with a nickel film. Graphene deposited via chemical vapor deposition formed into layers on both sides of the film, one on the exposed top side, and one on the underside, sandwiched between nickel and glass. Peeling the nickel and the top layer of graphene left intervening layer of graphene behind on the glass. While the top graphene layer could be harvested from the foil as in earlier methods, the bottom layer was already in place on the glass. The quality and purity of the attached layer was not assessed.

Copper

An improvement of this technique employs copper foil; at very low pressure, the growth of graphene automatically stops after a single graphene layer forms. Arbitrarily large films can be created. The single layer growth is also due to the low concentration of carbon in methane. Larger hydrocarbons such as ethane and propane produce bilayer coatings. Atmospheric pressure CVD growth produces multilayer graphene on copper (similar to nickel). Ballistic transport has also been observed in the graphene grown on copper.

Sodium Ethoxide Pyrolysis

Gram-quantities of graphene were produced by the reduction of ethanol by sodium metal, followed by pyrolysis of the ethoxide product and washing with water to remove sodium salts.

Silicon/Germanium/Hydrogen

A normal silicon wafer coated with a layer of germanium (Ge) dipped in dilute hydrofluoric acid strips the naturally forming germanium oxide groups, creating hydrogen-terminated germanium. Chemical vapor deposition deposits a layer of graphene on top. The graphene can be peeled from the wafer using a dry process and is then ready for use. The wafer can be reused. The graphene is wrinkle-free, high quality and low in defects.

Nanotube Slicing

Graphene can be created by cutting open carbon nanotubes. In one such method multi-walled carbon nanotubes are cut open in solution by action of potassium permanganate and sulfuric acid. In another method graphene nanoribbons were produced by plasma etching of nanotubes partly embedded in a polymer film.

Carbon Dioxide Reduction A highly exothermic reaction combusts magnesium in an oxidation-reduction reaction with carbon dioxide, producing a variety of carbon nanoparticles including graphene and fullerenes. The carbon dioxide reactant may be either solid (dry-ice) or gaseous. The products of this reaction are carbon and magnesium oxide. U.S. Pat. No. 8,377,408 was issued for this process.

Spin Coating

In 2014, carbon nanotube-reinforced graphene was made via spin coating and annealing functionalized carbon nanotubes. The resulting material was stronger, flexible and more conductive than conventional graphene.

Supersonic Spray

Supersonic acceleration of droplets through a Laval nozzle was used to deposit small droplets of reduced graphene-oxide in suspension on a substrate. The droplets disperse evenly, evaporate rapidly and display reduced flake aggregations. In addition, the topological defects (Stone-Wales defect and C 2 vacancies) originally in the flakes disappeared. The result was a higher quality graphene layer. The energy of the impact stretches the graphene and rearranges its carbon atoms into flawless hexagonal graphene with no need for post-treatment.

The following table provides exemplary characteristics of a graphene compound which has been tested by the inventors.

| | |
|---|---|
| Density (Kg/m3) | 1900 |
| Speed of sound (m/s, longitudinal wave) | 700 |
| Acoustic Impedance (Mega Rayls) | 1.3 |
| Thermal Conductivity, in plane (W/m*° K) | 600-1000 |
| Specific Heat @ 25° C. (J/g° K) | 0.7 |
| EMI Shielding dB@1.0 GHz | 50 |
| Surface Electrical Resistivity (Ω/sq) | 0.06 |
| Thickness (μm) | 20-50 |

For a comprehensive bibliography on graphene, reference can be made to quotations that can be found on WIKIPEDIA. See also Science 306, 666 (2004) and Nature 438, 197 (2005) by K. S. Novoselov, A. K. Geim et al., "Scientific Background on the Nobel Prize in Physics 2010" compiled by the Class for Physics of the Royal Swedish Academy of Sciences, 5 Oct. 2010, "Introduction to the Physical Properties of Graphene", Jean-Noel Fuchs, Mark Oliver Goerbig, Lecture Notes 2008 freely available on the internet at the address http://users.Ips.u-psud.fr/GOERBIG/CoursGraphene2008.pdf, "Graphene and Graphene Oxide: Synthesis, Properties and Applications", Y. Zhu, S. Murali, W. Cai, X. Li, JiWon Suk, J. R. Potts, R. Ruoff, Advanced Materials, 2010, XX, 1-19.

Graphene is currently used for thermal management and high-flux cooling of electronic devices and circuits (see for example US patent published application 20100085713), but its acoustic properties were not considered up to now. These properties have been studied by the inventors and found particularly suitable for realizing a heat drain device within an ultrasound array transducer structure. It is not only the low acoustic impedance that allows to use a layer of graphene as if it were one of the traditional matching layers, but also its behaviour as good acoustical dumping material that allows to use it as a filler of commonly used backing material. Backing of a probe is very critical because, if the material used is not properly selected, would be responsible of image artifacts due to acoustic impedance mismatch or internal reflection and scattering. The inventors studied these aspects. For example a graphite-polyurethane compound was tested which showed good heat drain performances, but developed image artifacts. Graphene surprisingly showed an incredible improvement both as thermal conductor and as acoustic impedance matching element.

Graphene was also found particularly useful as barrier to liquids due to its chemical and physical characteristics. It was, in fact, found by the inventors that this material acts as a good chemical barrier to alcohol with results comparable to Kapton. Alcohol, and disinfectants in general, pose serious problems in ultrasound probes because tend to penetrate the acoustic stacks and attack the matching layers with a progressive loss of performance. Using graphene as first matching layer would thus be beneficial also for this aspect.

Although the invention has been mainly disclosed with reference to a diagnostic probe, the skilled person would appreciate that its teachings can find applications also in therapy and in the more general field of non destructive testing. Particularly in the therapy field like HIFU, the structure of the array stack is different as it is mainly formed by annular elements, but also in this case a graphene-based layer can be placed in front and/or in the rear of such elements as well as laterally and, more in general, in any position heat accumulates and thus can be drained. Also in this case a PCM can be used as heat converter to temporarily store heat, alone or in combination with an active cooling system.

All without departing from the guiding principle of the invention disclosed above and claimed below.

The invention claimed is:

1. In an ultrasound probe having a probe housing that encloses a transducer assembly, a heat storing device comprising Phase Change Material (PCM) able to absorb heat maintaining the temperature constant, wherein the heat storing device comprises graphene and is disposed in an area within the probe housing;
   wherein the heat storing device comprises a composite material including a PCM and a filler charged with graphene, and
   wherein the filler is a resin, such as an epoxy resin, charged with graphene, the PCM being micro-encapsulated by such graphene-charged resin.

2. Heat storing device according to claim 1, wherein the heat storing device is configured to be interspersed in the probe housing in any position and without specific sites or receptacles to host the composite material due to its micro-encapsulation.

3. Heat storing device according to claim 1, wherein the heat storing device is an organic reversible PCM that accumulates heat in the form of latent heat while changing phase from solid to liquid and releases accumulated heat when changing phase from liquid to solid.

4. Heat storing device according to claim 1, wherein the heat storing device is disposed in a rear part of the probe housing.

5. Heat storing device according to claim 1, wherein the heat storing device is a filling material disposed in a rear part of the probe housing.

6. Heat storing device according to claim 5, wherein the filling material is arranged to fill available spaces inside the probe housing to temporarily store heat drained away from the transducer assembly.

7. In an ultrasound probe having a probe housing that encloses a transducer assembly, a heat storing device comprising Phase Change Material (PCM) able to absorb heat maintaining the temperature constant, wherein the heat storing device comprises graphene and is disposed wherein the heat storing device is disposed externally to the probe housing;
- wherein the heat storing device comprises a composite material including a PCM and a filler charged with graphene
- wherein the filler is a resin, such as an epoxy resin, charged with graphene, the PCM being micro-encapsulated by such graphene-charged resin.

8. Heat storing device according to claim 7, wherein the heat storing device is disposed relative to a cable connected to the probe housing.

\* \* \* \* \*